United States Patent
Klaveness et al.

[11] Patent Number: 5,574,097
[45] Date of Patent: Nov. 12, 1996

[54] CHEMICAL COMPOUNDS

[75] Inventors: Jo Klaveness, Oslo; Keith Redford, Hagan; Jan Solberg, Eiksmarka; Per Strande, Oslo, all of Norway

[73] Assignee: Nycomed Imaging AS, Oslo, Norway

[21] Appl. No.: 290,875

[22] PCT Filed: Mar. 5, 1993

[86] PCT No.: PCT/GB93/00469
 § 371 Date: Jan. 10, 1995
 § 102(e) Date: Jan. 10, 1995

[87] PCT Pub. No.: WO93/18070
 PCT Pub. Date: Sep. 16, 1993

[30] Foreign Application Priority Data

Mar. 6, 1992 [GB] United Kingdom ............... 9204918

[51] Int. Cl.⁶ ........................................ C08F 8/00
[52] U.S. Cl. ........................... 525/61; 526/304; 526/321; 526/323.1; 526/323.2; 528/59; 528/271; 528/296; 536/55.1
[58] Field of Search ................. 525/61; 526/304, 526/321, 323.1, 323.2; 536/55.1; 528/59, 271, 296

[56] References Cited

U.S. PATENT DOCUMENTS 4,356,166  10/1982  Peterson.
4,741,956  5/1988  Thaler.

FOREIGN PATENT DOCUMENTS 0130935  1/1985  European Pat. Off..

OTHER PUBLICATIONS

CA: 118:125529, "Studies on Beaded Crosslinked Functionalized Phenyl Acrylate Copolymers," Narasimhaswamy et al., 1991.
CA:77:62754, "Adhesives Containing Benzoyloxalkyl Groups", Sakuraki et al, 1972.

*Primary Examiner*—Bernard Lipman
*Attorney, Agent, or Firm*—Bacon & Thomas

[57] ABSTRACT

The invention relates to non-crosslinked non-polypeptide polymers containing biodegradable lipophilic side chains incorporating methylene diester units of the formula —[—CO—O—C($R^1R^2$)—O—CO—]—, where $R^1$ and $R^2$ each represents a hydrogen atom or a carbon-attached monovalent organic group or $R^1$ and $R^2$ together form a carbon-attached divalent organic group. The lipophilic moieties are biodegradatively cleavable to yield a water-soluble polymer.

21 Claims, 1 Drawing Sheet

CHEMICAL COMPOUNDS

This invention concerns biodegradable polymers, more particularly lipophilic polymers which are biodegradable to form water-soluble polymers.

Biodegradable polymers have long been used in the medical field, for example to provide biodegradable implant materials and delayed release drug delivery systems. They are now of wider interest in overcoming the problem of pollution by long-lived insert packaging materials, household articles, detergents and the like.

There is also a need for polymers which, when they wholly or partially break down by chemical or biological means, give reliably non-toxic and readily eliminable products.

In general, biodegradation commonly involves enzymic hydrolysis of particular chemical bonds in the polymer, notably ester, urethane or amide groups which are otherwise stable in the absence of enzymes; such hydrolysis may additionaly or alternatively be effected by the presence of acids or bases. Thus, for packaging materials, aliphatic polyesters such as polycaprolactone, polyethylene adipate and polyglycolic acid are candidate materials although polyethylene terephthalate, which is very widely used in textiles and fibres, is resistant to biodegradation.

In the medical field, resorbable polymers are of interest for sutures and in wound closure, resorbable implants in the treatment of osteomyelitis and other bone lesions, tissue stapling and mesh tamponades, anastomosis as well as drug delivery systems and diagnostics. In these fields, polylactic acid, polyglycolic acid, poly (L-lactide-co-glycolide), polydioxanone, poly (glycolide-cotrimethylene carbonate), poly (ethylene carbonate), poly (iminocarbonates), polyhydroxybutyrate, poly (amino acids), poly (ester-amides), poly (orthoesters) and poly (anhydrides) have all been proposed (T. H. Barrows, Clinical Materials 1 (1986), pp. 233–257) as well as natural products such as polysaccharides. U.S. Pat. No. 4,180,646, in particular, describes novel poly (orthoesters) for use in a very wide range of products.

In our co-pending International Patent Application No. WO92/04392 the contents of which are incorporated herein by reference, we describe a broad range of polymers characterised in that they contain optionally substituted methylene diester units of the formula (I)

(where $R^1$ and $R^2$ each represent a hydrogen atom or a carbon-attached monovalent organic group or $R^1$ and $R^2$ together form a carbon-attached divalent organic group). Such units are particularly rapidly degraded by common esterase enzymes but are stable in the absence of enzymes. They may be attached not only to carbon-attached organic groups as in simple carboxylate esters but also to —O— atoms as in carbonate esters.

The aforementioned units of formula (I) are normally present in the polymer backbone, either as repeating units or as linking units between polymer sections, or are present in crosslinking groups between polymer chains. In this latter context one may, for example, convert a water-soluble long chain natural or synthetic non-biodegradable or slowly biodegradable substance, e.g. a protein such as gelatin or albumin, a polysaccharide or oligosaccharide, or a short chain polyacrylamide, into a water-insoluble but biodegradable form by crosslinking using crosslinking groups containing units of formula (I); this may reduce the cost of the product in comparison with polymers which contain units of formula (I) in the polymer backbone by reducing the relative content of the comparatively expensive units of formula (I).

While such crosslinked polymers have a wide variety of uses as described in the above-mentioned Application No. WO92/04392, their structure inevitably places some limitations on the processability of the polymers, since by virtue of their crosslinked nature they will generally be insoluble in organic as well as aqueous solvents and will not exhibit thermoplastic properties. Accordingly they cannot be subjected to conventional techniques such as solvent casting or melt processing.

The present invention is based on our finding that it is possible to prepare substantially uncrosslinked (e.g. linear) polymers containing biodegradable lipophilic side chains, incorporating methylene diester units of formula (I), in such a way that the polymers combine the advantages of being substantially water-insoluble (or of significantly reduced water-solubility) while being thermoplastic and soluble in a variety of organic solvents and being biodegradable to give water-soluble (and therefore readily dispersible and/or eliminable) degradation products, in particular a water-soluble polymer generated by biodegradable cleavage of the lipophilic side chains.

In EP-A-0130935 there are described biodegradable esterified polypeptides of formula

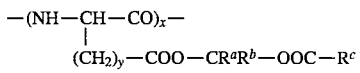

(in which $R^a$ and $R^b$ are alkyl groups or hydrogen atoms and $R^c$ is an optionally substituted aliphatic or aromatic group or $R^b$ is a hydrogen atom or an alkyl group and $R^a$ and $R^c$ together form a divalent group such as a dimethylene, vinylene or phenylene group, y is 1 or 2, and x is such that the molecular weight of the polymer is at least 5000) and copolymers thereof with other poly(amino acids) as delayed release carriers for drugs which may be mixed with or enclosed by the polymer. The first step in the biodegradation of such polymers is said to be cleavage of the side chain methylene diester groups to yield polymers containing units of formula

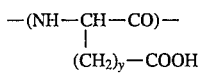

It is stated that such polymers will then be further degraded by peptidases to their component amino acid(s), which may be absorbed by the host to which the polymer/drug combination was administered. This pattern of degradation may be contrasted with that of the polymers of the present invention, where the polymers resulting from biodegradation of the lipophile-carrying methylene diester side chains are specifically chosen to be watersoluble so that they may be dispersed and/or eliminated without requiring further degradation.

A potential disadvantage of the polymers described in EP-A-0130935 is that the high level of hydrogen bonding exhibited by polypeptides will tend to cause them to have relatively high melting points, such that they may not be melt processable without undue degradation occurring. Furthermore, the peptide structures may be capable of causing allergenic reactions when used in vivo.

Figure 1:
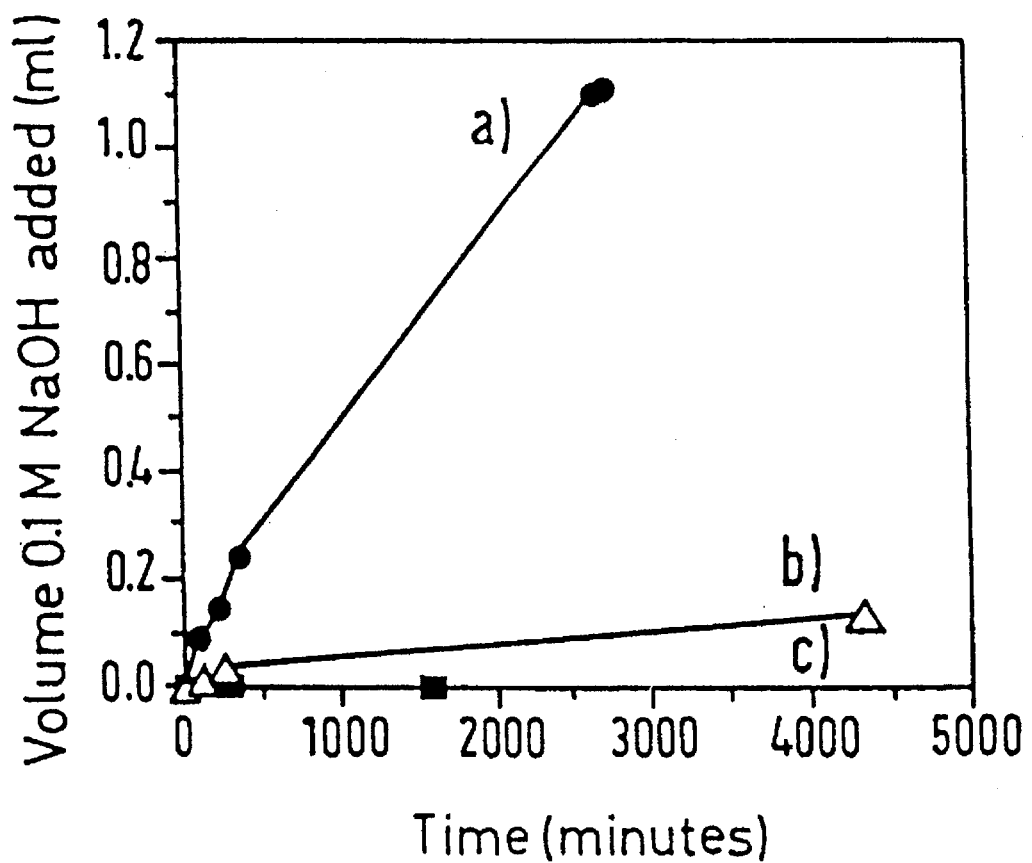
FIG. 1 represents a comparison of sodium hydroxide consumption between solutions containing polymer and esterase with solutions containing polymer alone.

According to one aspect of the present invention we provide biodegradable non-crosslinked polymers of low or zero water-solubilty comprising a non-polypeptide polymer backbone carrying side chains, at least a proportion of the said side chains containing lipophilic moieties bonded to the polymer backbone by way of methylene diester units of formula (I) as hereinbefore defined, whereby the said lipophilic moieties are biodegradatively cleavable to yield a water-soluble polymer.

As indicated above, each of the ester groupings of the methylene diester units of formula (I) may be either a carboxylate or a carbonate grouping. Polymers according to the invention may thus be represented as containing units of formula (II)

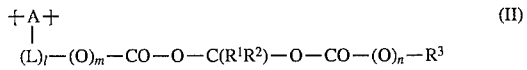

$$-\mathrm{A}-$$
$$|$$
$$(L)_l-(O)_m-CO-O-C(R^1R^2)-O-CO-(O)_n-R^3 \quad (II)$$

wherein A represents a repeating unit of a non-polypeptide polymer backbone chain; L represents an optional linking group (i.e. 1 is zero or 1); m and n, which may be the same or different, are each zero or 1; $R^1$ and $R^2$ are as hereinbefore defined; and $R^3$ represents a lipophilic organic group.

Biodegradation of the methylene diester groupings in polymers containing units of formula (II) will in general take place by enzymic hydrolytic cleavage of the bonds linking the group $-O-C(R^1R^2)-O-$ to the adjacent carbonyl groups, normally yielding an aldehyde or ketone of formula $R^1-CO-R^2$. The nature of the other degradation products will vary according to whether each of m and n is zero or 1; thus if m is zero a carboxyl group-containing water-soluble polymer with units of formula (III)

$$-\mathrm{A}-$$
$$|$$
$$(L)_l-COOH \quad (III)$$

(where A, L and 1 are as hereinbefore defined) will normally be formed, whereas if m is 1 the hypothetically formed carbonic acid group will generally eliminate carbon dioxide to yield a hydroxyl group-containing water-soluble polymer with units of formula (IV)

$$-\mathrm{A}-$$
$$|$$
$$(L)_l-OH \quad (IV)$$

(where A, L and 1 are as hereinbefore defined), while products $R^3-COOH$ and $R^3-OH$ will similarly be formed depending as to whether n is zero or 1.

Factors influencing the water solubility of polymeric degradation products containing units of formula (III) or (IV) include the nature of the repeating units A and any comonomer units which may be present, the length of any linking group L, and the overall chain length of the polymer, which in general is preferably such that the molecular weight of the biodegradable polymer does not exceed about 2,000,000. Polymers with lower molecular weight may be advantageous in, for example, applications where a high level of biodegradability is required. Thus, for example, it may be preferred that polymer systems designed for use in vivo, e.g. as drug delivery systems or diagnostic aids for parenteral administration, have a molecular weight not exceeding about 40,000.

Repeating units A and any comonomer units in polymers according to the invention are preferably comparatively short, e.g. containing up to 10, e.g. 1–6 carbon atoms and optionally interrupted by one or more heteroatoms selected from oxygen, nitrogen and sulphur and/or substituted by one or more substituents comprising such heteroatoms (e.g. as in oxo, hydroxy and amino groups). Where hydrophilic groups are included in the repeating units A and/or any comonomer units, the size of these units need not be limited and possible units thus include polyoxyethylene (e.g. as in polyoxyethylene esters of methacrylic acid).

Any linking groups L are preferably of short length and include, for example, $C_{1-3}$ alkylene groups such as methylene, ethylene or propylene optionally terminating in and/or (where appropriate) interrupted by, for example, oxy, carbonyl, oxycarbonyl, imino or imino-carbonyl groups. Where polar groupings such as oxygen atoms or imino groups are present in the linking groups may be longer, e.g. containing up to 10 carbon atoms without unduly inhibiting water solubility. Suitable polymeric degradation products thus include, for example, polyvinyl alcohol, polyacrylic acid, polymethacrylic acid, polyhydroxyalkyl acrylates and methacrylates such as poly(2-hydroxyethyl acrylate), polysaccharides, polyesters, polyethers such as polyoxyethylenes and polyoxypropylenes, polyacrylamides and polymethacrylamides such as poly(N-hydroxyalkyl) acrylamides and methacrylamides (e.g. poly N-(2-hydroxypropyl)methacrylamide), polyamides, polyurethanes and epoxy polymers..

In general the polymeric degradation products of biodegradable polymers according to the invention, by virtue of their water solubility, need not themselves be biodegradable; they may thus, for example, be polyolefinic. The invention therefore includes polymers containing units of formula (II) in which A is a repeating unit of a polyolefin, for example ethylene or propylene. It will be appreciated that polymers of this type may be prepared by free radical polymerisation techniques with comparative ease and economy, in contrast with the more complex polypeptide synthesis techniques needed to prepare polymers such as those described in EP-A-0130935.

In the biodegradable polymers according to the invention at least a proportion of the repeating units should have side chain units of formula

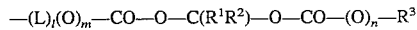

$$-(L)_l(O)_m-CO-O-C(R^1R^2)-O-CO-(O)_n-R^3$$

as defined for formula (II) attached to the polymer chain; it will be appreciated that the precise level of substitution may be varied, e.g. by use of copolymerisation or partial esterification techniques as described in greater detail hereinafter, to modify as desired the solubility parameters for both the biodegradable polymer and the degradation polymer product.

$R^1$ and $R^2$ (when other than hydrogen) and $R^3$ in side chain units of the above formula may, for example, each be a carbon-attached hydrocarbyl or heterocyclic group, for example having 1–20 carbon atoms, e.g. an aliphatic group such as an alkyl or alkenyl group (preferably having up to 10 carbon atoms), a cycloalkyl group (preferably having up to 10 carbon atoms), an araliphatic group such as an aralkyl group (preferably having up to 20 carbon atoms), an aryl group (preferably having up to 20 carbon atoms) or a heterocyclic group having up to 20 carbon atoms and one or more heteroatoms selected from O,S and N. Such a hydrocarbyl or heterocyclic grouping may carry one or more functional groups such as halogen atoms or groups of the formulae $-NR^4R^5$, $-CONR^4R^5$, $-OR^6$, $-SR^6$ and $-COOR^7$, where $R^4$ and $R^5$, which may be the same or different, are hydrogen atoms, acyl groups, or hydrocarbyl groups as defined for $R^1$ and $R^2$; $R^6$ is a hydrogen atom or an acyl group or a group as defined for $R^1$ or $R^2$ and $R^7$ is a hydrogen atom or a group as defined for $R^1$ or $R^2$. Where $R^1$ and $R^2$ represent a divalent grouping this may, for example, be an alkylidene, alkenylidene, alkylene or alkenylene group (preferably having up to 10 carbon atoms), which may carry one or more functional groups as defined above. The carbon chains of $R^3$ groups may, for example, be interrupted and/or terminated by heteroatoms such as O, N or S.

Aliphatic groups present as, for example, $R^1$, $R^2$ or $R^3$ may be straight or branched, saturated or unsaturated and include, for example, alkyl and alkenyl groups, e.g. methyl, ethyl, propyl, isopropyl, butyl, decyl or allyl groups. Araliphatic groups include (monocarbocyclic aryl)-alkyl groups, for example benzyl groups. Aryl groups include mono- or bi-cyclic aryl groups, for example phenyl, tolyl or naphthyl groups. Heterocyclic groups include 5- or 6-membered heterocyclic groups preferably having one heteroatom, for example furyl, thienyl or pyridyl groups. Halogen atom substituents may, for example, be chlorine, bromine or iodine.

The nature and size of $R^1$, $R^2$ and $R^3$ will influence both the level to which polymers containing units of formula (II) are rendered lipophilic and thus insolubilised with respect to water and the rate at which the side chain is biodegradably cleaved. Thus large and/or bulky groups will tend to reduce the rate of biodegradation through steric hindrance, while increasing the lipophilicity of the polymer. In one useful category of side chain $R^1$ and $R^2$ are each selected from hydrogen atoms and $C_{1-4}$ alkyl groups such as methyl, and $R^3$ represents a lower alkyl group, e.g. preferably containing 1–20 carbon atoms; such side chains combine substantial degrees of lipophilicity and biodegradability.

It will be appreciated that both the backbones and side chains of polymers according to the invention should be selected so that their degradation products are bioacceptable, in particular that they are non-toxic. In the case of polymers intended to be used for medical purposes the degradation products should also be physiologically acceptable; thus $R^1$, $R^2$, $R^3$, A and any linking group L should be such that the compound $R^1$—CO—$R^2$, polymers containing units of formula (III) or (IV) and products of formula $R^3$—COOH or $R^3$—OH are physiologically acceptable and readily dispersible and eliminable, preferably all being water-soluble. Carbon dioxide liberated by cleavage of any carbonate groupings present will normally be physiologically acceptable; its generation may be functionally desirable in some applications of polymers according to the invention.

The polymers of the invention may be prepared in any convenient way, for example by either (A) reaction of a preformed water-soluble polymer with a reagent serving to introduce the desired lipophilic methylene diester side chain, or (B) polymerisation of a functional monomer which carries the desired lipophilic methylene diester side chain.

Process (A) may be effected by, for example, reaction of a polymer having pendant alcoholic hydroxyl groups (e.g. polyvinyl alcohol, a polyhydroxyalkyl acrylate or a polysaccharide) with a compound of formula (V)

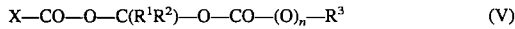

X—CO—O—C($R^1R^2$)—O—CO—(O)$_n$—$R^3$   (V)

(where $R^1$, $R^2$, $R^3$ and n are as hereinbefore defined and X represents a leaving group such as halogen atom, e.g. fluorine, chlorine, bromine or iodine). Reagents of formula (V) may, for example, be prepared as described by Folkmann and Lund, *Synthesis* 1990, 1159. Such reactions, which will yield polymers containing units of formula (II) in which m is 1, are conveniently effected in solution, for example in a solvent such as tetrahydrofuran, in the presence of a weakly nucleophilic base such as pyridine. A catalytic amount of a tertiary amine such as 4-dimethylaminopyridine may also be employed. The number of polymer hydroxyl groups which are reacted to form the desired lipophilic methylene diester groups may be controlled by appropriate choice of factors such as reagent quantities and reaction time and temperatures to affect the final hydrophilic-lipophilic balance of the lipophilised polymer. The product may be purified by standard techniques such as solvent extraction and/or dissolution/reprecipitation.

Alternatively, process (A) may be effected by reaction of a polymer having pendant carboxyl groups (e.g. polyacrylic acid or polymethacrylic acid) with a compound of formula (VI)

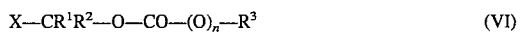

X—C$R^1R^2$—O—CO—(O)$_n$—$R^3$   (VI)

(where $R^1$,$R^2$,$R^3$, X and n are as hereinbefore defined). Such reactions, which will yield polymers containing units of formula (II) in which m is zero, are conveniently effected in solution, for example in a solvent such as N,N-dimethylformamide, in the presence of a strong base, for example an alkali metal alkoxide such as potassium t-butoxide. A catalytic amount of a crown ether such as 18-crown-6 may also be employed. Again the hydrophiliclipophilic balance of the polymer product can be controlled by appropriate selection of reaction parameters to determine the number of carboxyl groups which are reacted, and the product may be purified by conventional techniques.

Reagents of formula (VI) may be prepared by, for example, reaction of an aldehyde or ketone of formula $R^1$—CO—$R^2$ with an acid halide or haloformate ester of formula $R^3$—(O)n—CO—X, e.g. in the presence of a catalyst such as zinc chloride or pyridine.

Process (A) may also be effected by, for example, reaction of a polymer carrying functional groups such as epoxy groups with a reagent containing the desired lipophilic methylene diester grouping and having a terminal grouping reactive with such functional groups; terminal groups reactive with epoxy groups include amino, hydroxyl and carboxy groups. Similarly, the latter groups may be present in the initial polymer and the reagent may carry a terminal epoxy group.

It is generally preferred that polymer starting materials employed in process (A) have a molecular weight of not more than about 2,000,000.

Process (B) may be effected using any monomers which can be polymerised or copolymerised to form non-crosslinked polymers and which possess one or more substituents which do not participate in the polymerisation and which may be derivatised prior to polymerisation to introduce the desired lipophilic methylene diester grouping. Free radical, condensation and ionic polymerisation techniques may be employed.

Free radical polymerisation may, for example, be effected using carboxy group-containing monomers such as acrylic acid or methacrylic acid derivatised by reaction with a compound of formula (VI) or by using hydroxyl group-containing monomers such as 2-hydroxyethyl acrylate or N-(2-hydroxypropyl)methacrylamide derivatised by reaction with a compound of formula (V). Alternatively hydroxyl group-containing monomers may be reacted with a compound of formula (VII)

X—CO—O—C($R^1R^2$)—X   (VII)

(where $R^1$,$R^2$ and X are as hereinbefore defined) and the resulting product reacted with an appropriate salt of a carboxylic acid $R^3$—COOH.

Free radical polymerisation may also be effected using vinyl carbonate esters of formula $$CH_2=CH-O-CO-O-C(R^1R^2)-O-CO-(O)_n-R^3 \quad (VIII)$$

(where n, $R^1$, $R^2$ and $R^3$ are as defined above). Such monomers, for example having n=0, may be prepared by reaction of vinyl chloroformate with an aldehyde or ketone $R^1R^2C=O$ in the presence of a catalytic amount, for example, pyridine or a Lewis acid, to give an optionally substituted chloromethyl vinyl carbonate of formula (IX)

$$CH_2=CH-O-CO-O-C(R^1R^2)-Cl \quad (IX)$$

(where $R^1$ and $R^2$ are as defined above), followed by reaction with e.g. an appropriate salt of a carboxylic acid $R^3$—COOH, preferably in the presence of a catalytic amount of a suitable crown ether. It will be appreciated that compounds (VIII) may formally be regarded as "vinyl alcohol" derivatised by a compound of formula (VII). Polymers derived therefrom should accordingly be enzymatically biodegradable to polyvinyl alcohol.

Conventional bulk, solution, emulsion and suspension polymerisation techniques may be employed. The molecular weight of the polymer product, which preferably should not exceed about 2,000,000, may be controlled by the use of chain transfer agents such as mercaptans, from which the growing polymer chain can abstract a proton leading to chain termination and formation of a sulphur radical which will initiate a new polymer chain; the molecular weight of the polymer will thus be governed by the type and concentration of the transfer agent.

Appropriate vinyl monomers, e.g. having a carbonyl group adjacent to the vinyl group, as in acrylic or methacrylic esters, for example prepared as described above, may also be subjected to ionic polymerisation techniques, both anionic and cationic; such techniques are particularly suited to the production of well-defined molecular weight polymer, especially comparatively low molecular weight materials.

Condensation polymerisation may be effected using a wide range of appropriately functionalised monomers, examples of which may be represented by formulae (X) and (XI)

$$
\begin{array}{c}
Y \\
| \\
(CH_2)_a \\
| \\
CH-(O)_m-CO-O-C(R^1R^2)-O-CO-(O)_n-R^3 \\
| \\
(CH_2)_b \\
| \\
Y
\end{array}
\quad (X)
$$

$$
\begin{array}{c}
Y \\
| \\
(CH_2)_a \\
| \\
CH-(O)_m-CO-O-C(R^1R^2)-O-CO-(O)_n-R^3 \\
| \\
(CH_2)_b \\
| \\
CH-(O)_m-CO-O-C(R^1R^2)-O-CO-(O)_n-R^3 \\
| \\
(CH_2)_c \\
| \\
Y
\end{array}
\quad (XI)
$$

(where $R^1, R^2, R^3$, m and n are as hereinbefore defined, Y is a reactive grouping such as carboxy, hydroxyl or an epoxy group such as 2,3 epoxypropyloxy, and a, b and c may each be zero or a small integer such as 1,2 or 3). In formula (XI) the groups $R^1$, $R^2$ and $R^3$ and m and n may be the same or different in the two side chains. Such monomers may be employed in conventional condensation reactions with, as appropriate, reagents such as dicarboxylic acids, dialcohols, diamines, di(acid chlorides), diisocyanates and bisepoxy compounds to yield polymers such as polyesters, polyamides, polyurethanes and epoxy polymers. The molecular weight of the polymer product may be controlled by selection of appropriate reaction times, temperatures etc and/or by use of monofunctional chain terminators.

Where appropriate, polymers according to the invention may be prepared using emulsion polymerisation techniques; this may be of particular value where, for example, it is desired to prepare the polymers in the form of monodisperse particles. Methods of emulsion polymerisation to produce particles, especially monodisperse particles, are described in EP-A-0003905, EP-A-0091453, EP-A-0010986 and EP-A-0106873.

Polymers according to the invention find utility in, for example, surgical implants such as sutures, soft tissue prostheses, sponges, films (e.g. artificial skin) or wound dressings (e.g. hydrogel sheets), flexible sheet materials and articles such as containers formed therefrom, the manufacture of biodegradable delayed release formulations for drugs or agricultural chemicals, and horticultural aids such as water-retaining "mulch" sheeting and plant containers. Such usages and the polymers shaped for use therein comprise further features of the invention. For use as prostheses, the shaped polymers may advantageously carry heparin, at least on the surface thereof.

As discussed above, the linear nature of the polymers of the invention enhances their processability. Thus by virtue of their thermoplasticity they may be melt processed by standard techniques such as injection moulding, extrusion and film blowing. Solutions of the polymers in appropriate organic solvents may be used in, for example, coating of tablets, casting of films and spinning of fibres.

Where a polymer of the invention is to be used as a biodegradable delayed release agent, the active material may be contained within a shell of the biodegradable polymer, e.g. in a capsule or in microspheres, or it may be physically incorporated during polymerisation so that it is uniformly distributed within the polymer and is released during biodegradation. Alternatively, the active material may comprise all or part of any of the groups $R^1$, $R^2$ or $R^3$ and thus be released by the enzymatic cleavage. Typical drugs for incorporation in delayed release formulations include steroids, contraceptives, antibacterials, narcotics-antagonists and anti-tumour drugs.

The polymers of the invention, when of appropriately short chain length, may be used as plasticisers for other polymers. Where the polymers of the invention are biodegradable, degradation of the plasticiser thus either breaks up the integrity of the material or opens it up to attack by enzymes.

Biodegradable polymer particles according to the invention can also advantageously be used for diagnostic purposes. Thus an X-ray contrast agent, which will normally be a poly-iodo aromatic compound, may form all or part of the group $R^3$ or $-C(R^1R^2)-$ so that it is liberated and safely eliminated from the body on biodegradation. Such particles may be used for visualisation of the liver and spleen since they are trapped in the reticuloendothelial systems of those organs. The X-ray contrast agent may also be simply held physically in the polymers by being incorporated during polymerisation.

Polymer particles according to the invention may also contain paramagnetic, superparamagnetic or ferromagnetic substances which are of use in magnetic resonance imaging (MRI) diagnostics. Thus, submicron particles of iron or a magnetic iron oxide can be physically incorporated into the polymers during polymerisation to provide ferromagnetic or superparamagnetic particles. Paramagnetic MRI contrast agents principally comprise paramagnetic metal ions, such as gadolinium ions, held by a chelating agent which prevents their release (and thus substantially eliminates their toxicity). Such chelating agents with complexed metal ions may be physically held in the polymers by being present during polymerisation or the groups $R^1$, $R^2$ and $R^3$ may comprise suitable chelating groups. In general many such chelating agents are poly-amino polycarboxylic acids such as diethylene triamine pentaacetic acid (R. B. Lauffer, Chem. Rev. 87 (1987), pp. 901–927).

Polymer particles of the invention may also contain ultrasound contrast agents such as heavy materials, e.g. barium sulphate or iodinated compounds such as the X-ray contrast agents referred to above, to provide ultrasound contrast media. Polymers according to the invention may also be used to prepare gas-containing porous polymer microparticles and gas-containing microballoons encapsulated by polymer coatings, both of which may be useful as ultrasound contrast agents.

The following Examples are given by way of illustration only.

GENERAL

Methacrylic acid was distilled under high vacuum to remove the stabiliser. 2,2'-Azobisisobutyronitrile (AIBN) thermal initiator was purified by recrystallisation from methanol.

All reactions were carried out under $N_2$.

Size Exclusion Chromatography (SEC):

Pump: Knauer HPLC pump 64

Detector: Knauer Differential refractometer

Columns: Polymer Laboratores PL gels columns in series Pore sizes $10^4$Å, 500Å, and 100Å, particle size 5μm, length 30, 30 and 60 cm respectively.

Solvent: THF

Calibration: Polystyrene standards (Polymer Laboratories)

Flow rate marker: Toluene

Software: Polymer Laboratores GPC/SEC software version 5.10

Mw: weight average molecule weight

Mn: number average molecule weight

Mw/Mn: polydispersity

Mp: molecular weight at maximum detector response

List of abbreviations

Tg: glass transition temperature

TBA-OH: tetrabutylammonium hydroxide

TBA: tetrabutylammonium

AIBN: 2,2'-azobisisobutyronitrile $SO_2Cl_2$: sulfuryl chloride

EtSCl: ethanesulfenyl chloride

DBU: 1,8-diazabicyclo[5.4.0]undec-7-ene(1,5-5)

$MgSO_4$: magnesium sulphate

THF: tetrahydrofuran

DMF: N,N-dimethylformamide

EXAMPLE 1

Butyl Methacryloyloxymethyl Carbonate

To a solution of chloromethyl chloroformate (2.84 g, 22.0 mmol ) and pyridine (1.78 ml, 22.0 mmol ) in methylene chloride (24 ml), n-butanol (1.84 g, 20.0 mmol) was added at 0° C. After 30 minutes at 0° C. and 21 hours at 25° C. the reaction mixture was washed with aqueous hydrochloric acid (1M, 10 ml), aqueous saturated sodium hydrogen carbonate (10 ml) and water (10 ml). The solvent was removed under reduced pressure after drying ($MgSO_4$), giving 2.66 g (80%) of the intermediate n-butyl chloromethyl carbonate as a crude product. $^1$H NMR (60 MHz, $CDCl_3$) δ:0.86 ($CH_3$—$CH_2$, m), 1.40 ($CH_2$—$CH_2$, m), 4.15 ($CH_2$—O, t), 5.63 ($CH_2$—Cl, s).

The intermediate n-butyl chloromethyl carbonate (2.5 g 15.0 mmol) was dissolved in dimethyl formamide (80 ml), and potassium methacrylate (1.77 g, 15.0 mmol) was added together with a catalytic amount of 18-crown-6 (0.2 g, 7.5 mmol). After 3 days at 25° C. the solvent was removed under reduced pressure, cholorform (30 ml) and water (20 ml) were added and the product was extracted into chloroform. The solvent was removed under reduced pressure after drying ($MgSO_4$). Flash chromatography gave 1.96 g (61%) of butyl methacryloyloxymethyl carbonate.

$^1$HNMR (300 MHz, $CHCl_3$) δ:0.99 ($\underline{CH_3}$—$CH_2$,t),1.47($\underline{CH_2}$—$CH_2$,m), 1.72($\underline{CH_2}$—$CH_2$,m),2.01($CH_3$,s) ,4.25($CH_2$—O,t) ,5.74(H—C=,m), 5.89($OCH_2O$, s),6.27 (H-C=,m). $^{13}$CNMR(75 MHz,$CDCl_3$) δ13.47 ($CH_3$), 17.97,18.71,30.36($CH_3$ and $CH_2$x2) ,68.46($CH_2O$) ,82.07 (O—$CH_2$—O) ,127.46 ($CH_2$=) ,135.05(C=) , 153.89 (C=O), 165.50(C=O).

EXAMPLE 2 a) Polymer from Butyl Methacryloyloxymethyl Carbonate

The monomer butyl methacryloyloxymethyl carbonate (350 mg) was dissolved in THF (2 ml). AIBN (1 mg) was added as a free radical initiator. The solution was polymerised at 50° C. for 5 hours. The product was recovered by precipitation into water. Size Exclusion Chromatography (SEC): Mw=165000, Mn=70000, Mw/Mn=2.3.

b) Polymer from Butyl Methacryloyloxymethyl Carbonate

A solution of butyl methacryloyloxymethyl carbonate (1.0 g) in DMF was heated to 60° C. and AIBN (0.005 g, 0.03 mol) was added. After 24 hours the reaction mixture was cooled and the polymer solution added dropwise to a stirred excess of methanol. The polymer was filtered and washed with methanol and water, and dried under reduced pressure.

IR (KBr): 1763 (C=O) $cm^{-1}$. $^1$H NMR (300 MHz, $CDCl_3$): δ 0.90 (t, 3H, $CH_3$), 1.00 (m, 2H, $CH_2$), 1.39 (m, 2H, $CH_2$), 1.70 (m, 2H, $CH_2$), 1.90 (m, 3H, $CH_3$), 4.20 (t, 2H, $CH_2O$), 5.68 (s, 2H, $OCH_2O$). $^{13}$C NMR (75 MHz, $CDCl_3$): δ 13.54 ($CH_3CH_2$), 18.73 ($CH_2$), 30.39 ($CH_2$), 46.26 (C—$CH_3$), 69.72 ($CH_2O$), 83.67 (—$OCH_2O$—), 153.86 (C=O), 175.80 (C=O).

Differential scanning calorimetry (DSC) indicated that onset decomposition temperature was 239.9° C. (Tg was not observed). Thermal mechanical analysis indicated a glass transition temperature of 24.7° C. Size Exclusion Chromatography (SEC): Mw=60000, Mn=29000, Mw/Mn=2.1.

EXAMPLE 3

Copolymer from Butyl Methacryloyloxymethyl Carbonate and Acrylamide

The momoners butyl methacryloyloxymethyl carbonate (250 mg) and acrylamide (250 mg) were dissolved in THF (5 ml). AIBN (1 mg) was added as a free radical initiator.

The solution was polymerised at 60° C. for 2 hours. The product was recovered by precipitation into cold water.

EXAMPLE 4

General Procedure for Chloromethyl Carbonates

To a solution of chloromethyl chloroformate and the stated alcohol in methylene chloride (200 ml), pyridine was added at 0° C. After 20 min. at 0° C. and 21 hours at 25° C. the reaction mixture was washed with aqueous hydrochloric acid (1M, 10 ml), aqueous saturated sodium hydrogen carbonate (10 ml) and water (10 ml). The solvent was removed under reduced pressure after drying ($MgSO_4$), giving crude chloromethyl carbonate.

TABLE 1

| Example | Chloromethyl-chloroformate g, mmol | Alcohol, ROH R, (g, mmol) | Pyridine g, mmol |
|---|---|---|---|
| 4a | 25.01, 194 | $CH_3$ (5.64, 176) | 15.52, 194 |
| 4b | 15.81, 124 | $CH_3CH_2$ (5.20, 113) | >9.91, 124 |
| 4c | 20.01, 155 | $CH_3(CH_2)_9$, (22.25, 139) | 12.54, 157 |
| 4d | 20.02, 155 | $PhCH_2$, (15.23, 141) | 12.54, 157 | a) Methyl chloromethyl carbonate

The compound was obtained from chloromethyl chloroformate and methanol.

$^1$H NMR (60 MHz, $CDCl_3$) : δ 3.98 (s, 3H, $OCH_3$), 5.85 (s, 2H, $CH_2Cl$).

b) Ethyl chloromethyl carbonate

The compound was obtained from chloromethyl chloroformate and ethanol.

$^1$H NMR (60 MHz, $CDCl_3$): δ 1.25 (t, 3H, $CH_3$), 4.25 (q, 2H, $CH_2$), 5.70 (s, 2H, $OCH_2Cl$).

c) Decyl chloromethyl carbonate

The compound was obtained from chloromethyl chloroformate and decyl alcohol.

$^1$H NMR (60 MHz, $CDCl_3$) δ 0.90–1.50 (m, 19H, $CH_3$ and $CH_2$), 4.20 (m, 2H, $CH_2O$), 5.75 (s, 2H, $OCH_2Cl$).

d) Benzyl chloromethyl carbonate

The compound was obtained from chloromethyl chloroformate and benzyl alcohol.

$^1$H NMR (60 MHz, $CDCl_3$): δ 5.20 (s, 2H, $PhCH_2O$), 5.70 (s, 2H, $ClCH_2O$), 7.32 (s, 5H, Ph).

EXAMPLE 5

General Procedure for Methacryloyloxymethyl Carbonates

Potassium tert. butoxide was added to a solution of methacrylic acid in DMF (200 ml). Chloromethyl carbonate from Example 4 above was added to the resulting suspension. 18-crown-6 was then added and the reaction mixture was left with stirring at room temperature for 24 hours. The reaction mixture was filtered and the solvent was removed under reduced pressure. The residue was dissolved in chloroform (30 ml) and washed with saturated aqueous sodium hydrogen carbonate (10 ml) and water (20 ml). The organic phase was dried ($MgSO_4$) and the solvent removed under reduced pressure.

TABLE 2

| Example | Compound, (g, mmol) | Potassium methacrylate (g, mmol) | 18-crown-6 (g, mmol) | DMF (ml) |
|---|---|---|---|---|
| 5a | 4a, (9.67, 78) | 8.71, 78 | 1.01, 38 | 350 |
| 5b | 4b, (8.04, 60) | 6.73, 60 | 0.6, 23 | 300 |
| 5c | 4c, (30.61, 122) | 13.67, 122 | 2.5, 94 | 600 |
| 5d | 4d, (22.01, 110) | 13.64, 110 | 1.5, 57 | 550 | a) Methyl methacryloyloxymethyl carbonate

The compound was obtained from methyl chloromethyl carbonate and potassium methacrylate.

IR (KBr): 1772 (C=O, str.), 1737 (C=O, str.), 1635 (C=C, str.) cm$^{-1}$ $^1$H NMR (300 MHz, $CDCl_3$): δ 1.91 (s, 3H, $CH_3C$=), 3.79 (s, 3H, $CH_3O$), 5.64 (m, 1H, $CH_2$=) 5.80 (s, 2H, —$OCH_2O$—), 6.16 (m, 1H, $CH_2$=). $^{13}$C NMR (75 MHz, $CDCl_3$): δ 17.95 ($CH_3C$=), 55.13 ($CH_3O$), 82.18 (—$OCH_2O$—), 127.52 ($CH_2$=), 135.02 (C=) , 154.44 (C=O), 165.46 (C=O).

b) Ethyl methacryloyloxymethyl carbonate

The compound was obtained from ethyl chloromethyl carbonate and potassium methacrylate.

IR (KBr): 1772 (C=O, str. ) , 1736 (C=O, str.) , 1635 (C=C, str. ) cm$^{-1}$ $^1$H NMR (300 MHz, $CDCl_3$): δ 1.27 (t, 3H, $CH_3$) , 1.92 (s, 3H, $CH_3C$=), 4.23 (q, 2H, $CH_2$), 5.66 (m, 1H, $CH_2$=), 5.80 (s, 2H, —$OCH_2O$—), 6.20 (m, 1H, $CH_2$=). $^{13}$C NMR (75 MHz, $CDCl_3$): δ 15.70 $\underline{C}H_3CH_2$), 19.60 ($\underline{CH_3}C$=), 65.72 ($CH_2O$), 83.05 (—$OCH_2O$—), 127.76 ($CH_2$=), 135.40 (C=), 153.82 (C=O), 165.42 (C=O).

c) Decyl methacryloyloxymethyl carbonate

The compound was obtained from decyl chloromethyl carbonate and potassium methacrylate.

IR (KBr): 1772 (C=O, str.), 1763 (C=O, str.), 1635 (C=C, str. ) cm$^{-1}$ $^1$H NMR (300 MHz, $CDCl_3$): δ 0.90 (t, 3H, $CH_3$), 1.28 (m, 14H, $CH_2$), 1.72 (m, 2H, $CH_2$), 1.99 (s, 3H, $CH_3C$=), 4.21 (t, 2H, $CH_2O$), 5.70 (m, 1H, $CH_2$=) 5.86 (s, 3H, —$OCH_2O$—), 6.24 (m, 1H, $CH_2$=). $^{13}$C NMR (75 MHz, $CDCl_3$): δ 13.78 $CH_3$), 17.76 ($CH_3C$=), 22.76–31.55 ($CH_2$), 68.60 ($CH_2O$), 81.90 (—$OCH_2O$—), 127.28 ($CH_2$=), 134.86 (C=), 153.73 (C=O), 165.33 (C=O).

d) Benzyl methacryloyloxymethyl carbonate

The compound was obtained from benzyl chloromethyl carbonate and potassium methacrylate.

IR (KBr): 3077 (Ph), 1772 (C=O, str.), 1763 (C=O, str.), 1635 (C=C, str. ) cm$^{-1}$ $^1$H NMR (300 MHz, $CDCl_3$): δ 1.96 (s, 3H, $CH_3C$=), 5.22 (s, 2H, $CH_2O$), 5.70 (m, 1H, $CH_2$=), 5.87 (s, 3H, —$OCH_2O$—), 6.22 (m, 1H, $CH_2$=), 7.39 (s, 5H, Ph) . $^{13}$C NMR (75 MHz, $CDCl_3$): δ 17.96 ($CH_3C$=), 69.91 ($CH_2O$), 82.03 (—$OCH_2O$—), 127.41 ($CH_2$=), 128.32 (Ph), 134.78 (C=), 53.58 (C=O), 165.28 (C=O).

EXAMPLE 6

General Procedure for Polymerization of Methacryloyloxymethyl Carbonates

A solution of methacryloyloxymethyl carbonate (1.0 g) from Example 5 above in DMF (8.0 g) was heated to 60° C. and AIBN (0.005 g, 0.03 mmol) was added. After 24 hours the reaction mixture was cooled and the polymer solution added dropwise to a stirred excess of methanol (nonsolvent).

The polymer was filtered and washed with methanol and water, and dried under reduced pressure.

a) Polymer from methyl methacryloyloxymethyl carbonate

IR (KBr): 1763 (C=O, str.) cm$^{-1}$ $^1$NMR (300 MHz, CDCl$_3$): 67 1.00 (m, 2H, CH$_2$), 1.90 (m, 3H), 3.85 (s, 3H, CH$_3$O), 5.70 (s, 2H, OCH$_2$O). $^{13}$C NMR (75 MHz, CDCl$_3$): δ 46.35 (C—CH$_3$), 56.55 (CH$_3$O), 83.59 (—OCH$_2$O—), 154.41 (C=O), 175.50 (C=O).

Differential scanning calorimetry (DSC) indicated that Tg=59.8° C. and onset decoposition temperature was 242.2° C. Thermal mechanical analysis indicated a glass transition temperature of 59.9 ° C. Size Exclusion Chromatography (SEC): Mw=100000, Mn=59000, Mw/Mn=1.7.

b) Polymer from ethyl methacryloyloxymethyl carbonate

IR (KBr): 1763 (C=O, str.) cm$^{-1}$ $^1$H NMR (300 MHz, CDCl$_3$): δ 1.00 (m, 2H, CH$_2$), 1.32 (t, 3H, CH$_3$), 1.90 (m, 3H, CH$_3$), 4.25 (m, 2H, CH$_2$O), 5.70 (s, 2H, OCH$_2$O). $^{13}$C NMR (75 MHz, CDCl$_3$): δ 15.77 (CH$_3$CH$_2$), 46.35 (C—CH$_3$), 65.90 (CH$_2$O), 83.50 (—OCH$_2$O—), 153.69 (C=O), 175.80 (C=O).

Differential scanning calorimetry (DSC) indicated that Tg=35.9° C. and onset decomposition temperature was 260.9° C. Thermal mechanical analysis indicated a glass transition temperature of 31.2° C. Size Exclusion Chromatography (SEC): Mw=34000, Mn=20000, Mw/Mn=1.7.

c) Polymer from decyl methacryloyloxymethyl carbonate

IR (KBr): 1763 (C=O, str.) cm$^{-1}$ $^1$H NMR (300 MHz, CDCl$_3$): δ 0.90 (t, 3H, CH$_3$), 0.90 (m, 3H, CH$_2$), 1.30 (m, 14H, CH$_2$), 1.70 (m, 2H, CH$_2$), 1.90 (m, 2H), 4.19 (t, 2H, CH$_2$O), 5.66 (s, 2H, OCH$_2$O). $^{13}$C NMR (75 MHz, CDCl$_3$): δ 13.78 (CH$_3$), 22.34–31.57 (CH$_2$), 46.26 (C—CH$_3$), 68.70 (CH$_2$O), 83.67 (—OCH$_2$O—), 153.55 (C=O), 175.80 (C=O).

Differential scanning calorimetry (DSC) indicated that onset decomposition temperature was 232.9° C. (Tg was not observed). Thermal mechanical analysis indicated a glass transition temperature of −3.3° C. Size Exclusion Chromatography (SEC): Mw=160000, Mn=90000, Mw/Mn=1.7.

d) Polymer from benzyl methacryloyloxymethyl carbonate

IR (KBr): 3077 (Ph), 1763 (C=O, str.) cm$^{-1}$ $^1$H NMR (300 MHz, CDCl$_3$): δ 0.95 (m, 3H, CH$_3$), 1.90 (m, 2H), 5.25 (s, 2H, CH$_2$O), 5.75 (s, 2H, OCH$_2$O), 6,70 (s, 5H, Ph). $^{13}$C NMR (75 MHz, CDCl$_3$): δ 46.26 (—C—CH$_3$), 68.03(—OCH$_2$Ph), 82.02 (—OCH$_2$O—), 129.45 (Ph), 153.67 (C=O), 175.80 (C=O).

Differential scanning calorimetry (DSC) indicated that Tg=31.6° and onset decomposition temperature was 197.1° C. Thermal mechanical analysis indicated a glass transition temperature of 32.8° C. Size Exclusion Chromatography (SEC): Mw=92000, Mn=44000, Mw/Mn=2.1.

EXAMPLE 7

Free Radical Solution Polymerisation of Benzyl Methacryloyloxymethyl Carbonate Giving Low Molecular Weight Polymer A solution of benzyl methacryloyloxymethyl carbonate (0.5 g, 2.0 mmol) from Example 5d above in DMF (7.5 g) was heated to 60° C. and allyl mercaptan (0.0015 g, 0.02 mmol) together with AIBN (0.0025 g, 0.015 mmol) was added. After 24 hours the reaction mixture was cooled and the polymer solution added dropwise to a stirred excess of methanol (non-solvent). The polymer was filtered and washed with methanol and water and dried under reduced pressure.

Size Exclusion Chromatography (SEC): Mw=22000, Mn=14000, Mw/Mn=1.6.

EXAMPLE 8

Free Radical Solution Polymerisation of Ethyl Methacryloyloxymethyl Carbonate and Methacrylic Acid The monomer feed mixture consisting of ethyl methacryloyloxymethyl carbonate from Example 5b above and methacrylic acid in DMF (8.0 g) was heated to 60° C. and AIBN (0.005 g, 0.03 mol) added. After 24 hours the polymer solution was added dropwise to a stirred excess of chloroform (non-solvent), filtered and washed with more chloroform and dried under reduced pressure.

TABLE 3

| Example | Methacrylic acid (g, mmol) | Ethyl methacryloyloxymethyl carbonate (g, mmol) | Molar ratio methacrylic acid: 5b |
| --- | --- | --- | --- |
| 8a | 0.73, 8.48 | 0.25, 1.33 | 86:14 |
| 8b | 0.73, 8.48 | 0.17, 0.90 | 90:10 |
| 8c | 0.73, 8.48 | 0.14, 0.74 | 92:8 |
| 8d | 0.92, 10.7 | 0.08, 0.43 | 96:4 |

$^1$H NMR (200 MHz, CDCl$_3$): δ 1.10 (s, 6H, 2xCH$_3$), 1.27 (t, 3H, CH$_3$CH$_2$), 1.90 (s, 4H, 2xCH$_2$), 3.52 (bs, 1H, oH), 4.2 (m, 2H, CH$_3$CH$_2$), 5.72 (s, —OCH$_2$O—)

TABLE 4

| The solubility of each of the copolymers in hot and cold water. | | |
| --- | --- | --- |
| Example | Solubility (cold water) | Solubility (hot water) |
| 8a | None | None |
| 8b | None | None |
| 8c | None | Some |
| 8d | Complete* | Complete |

N.B. *Complete solubilisation only after a relatively long period of time undergoing dissolution.

EXAMPLE 9

Ethyl 1-chloroethyl Carbonate

To a solution of 1-chloroethyl chloroformate (23.16 g, 0.162 mol) and ethanol (7.45 g, 0.162 mol) in methylene chloride (200 ml), pyridine (12.82 g, 0.162 mol) was added at 0° C. After 10 min at 0° C. and 21 hours at 25° C. the reaction mixture was washed with aqueous hydrochloric acid (100 ml), aqueous saturated sodium hydrogen carbonate (100 ml) and water (100 ml). The solvent was removed under reduced pressure after drying (MgSO$_4$), giving 18.5 g (74%) of the intermediate ethyl chloroethyl carbonate as a crude product.

$^1$H NMR (60 MHz, CDCl$_3$): δ 1.30 (t, 3H, CH$_3$), 1.85 (d, 3H, CH$_3$CH), 4.25 (q, 2H, CH$_2$), 6.45 (q,1H, CH).

EXAMPLE 10

Ethyl 1-methacryloyloxyethyl Carbonate

Potassium tert. butoxide (3.70 g, 0.033 mol) was added to a solution of methacrylic acid (2.84 g, 0.033 mol) in DMF (100 ml). Ethyl 1-chloroethyl carbonate (5.08 g, 0.033 mol) from Example 9 above was added to the resulting suspension. 18-crown-6 (0.61 g, 2.3 mmol) was then added and the reaction mixture was left with stirring at room temperature for 3 days. The reaction mixture was filtered and the solvent was removed under reduced pressure. The residue was dissolved in chloroform (100 ml) and washed with saturated aqueous sodium hydrogen carbonate (50 ml) and water (50 ml). The organic phase was dried ($MgSO_4$) and the solvent removed under reduced pressure. Flash chromatography gave 2.50 g (38%) of the title product. (Adjusted for recovered starting material the yield was 75%).

$^1H$ NMR (60 MHz, $CDCl_3$): δ 1.30 (t, 3H, $CH_3$), 1.60 (d, 3H, $CH_3CH$), 2.00 (s, 3H, $CH_3C$=), 4.20 (q, 2H, $CH_2$), 5.70 (m, 1H, $CH_2$=), 6.25 (q, 1H, —$OCH(CH_3)O$—), 6.90 (m, 1H, $CH_2$=).

EXAMPLE 11

Free Radical Polymerisation of Ethyl 1-methacryloyloxyethyl Carbonate

AIBN (0.033 g, 0.02 mmol) was added to a solution of ethyl 1-methacryloyloxyethyl carbonate (0.504 g, 2.49 mmol) from Example 10 above in dry THF (8 ml) at 50° C. under a dry nitrogen atmosphere. After 7 hours the reaction mixture was cooled to 20° C., and polymer precipitated in methanol (50 ml) and the solution filtered. The resulting polymer was dissolved in THF, reprecipitated in methanol (70 ml) and filtered, resulting in 0.138 g of a white powder.

$^3H$ NMR (300 MHz, $CDCl_3$): δ 0.90 (m, 3H, $CH_3$), 1.25 (s, 3, $CH_3$), 1.45 (s, 3H, $CH_3$), 1.87 (m, 2H, $CH_2$), 4.15 (bs, 2H, $CH_2O$), 6.62 (bs, 1H, —$CHCH_3$).

Size Exclusion Chromatography (SEC): Mw=26500, Mn=18600, Mp=22000, Mw/Mn=1.43.

EXAMPLE 12

Polymer from Ethyl Methacryloyloxymethyl Carbonate, Emulsion Polymerisation

A solution of sodium dodecyl sulphate (0.056 g, 0.19 mmol) in water (20.5 ml) was heated to 60° C. under nitrogen atmosphere, before ethyl methacryloyloxymethyl carbonate (5.266 g, 28.00 mmol) from Example 6b above was added. The polymerisation was initiated with a potassium metabisulphite (53.4 mg, 0.24 mmol)/potassium persulphate (4.38 mg, 0.02 mmol) redox system. After 16 hours at 60° C., potassium persulphate (4.38 mg, 0.02 mmol) was added, and the polymerisation was permitted to proceed for another 3 hours at 60° C. and under nitrogen atmosphere before cooling to 20° C.

EXAMPLE 13

O-Acetoxymethyl-S-ethyl Carbonothioate

O-Chloromethyl-S-ethyl carbonothioate[1] (4.50 g, 0.028 mol) in DMF (20 ml) was added to a solution of potassium acetate (2.74 g, 0.028 mol) in THF (100 ml). 18-crown-6 (0.22 g, 0.84 mmol) was then added and the reaction mixture was left with stirring at room temperature for 3 days. The reaction mixture was filtered and the solvent was removed under reduced pressure. The residue was purified by flash chromatography (silicagel, chloroform) to give 4.23 g (85%) of the title product.

$^1H$ NMR (60 MHz, $CDCl_3$): δ 1.30 (t, 3H, $CH_3CH_2$), 2.20 (s, 3H, $CH_3C$=O), 2.95 (q, 2H, $CH_2CH_3$), 5.80 (s, 2H, $OCH_2O$).

EXAMPLE 14

Acetoxymethyl Chloroformate $SO_2Cl_2$ (2.43 g, 0.018 mol) was added to O-acetoxymethyl S-ethyl carbonothioate (3.15 g, 0.018 mol) from Example 13 above at 0°–5° C. with stirring during 15 min. followed by stirring at room temperature for 45 min. Evaporation of EtSCl at room temperature and 11 mmHg gave a colourless liquid. Yield: 2.44 g (89%).

$^1H$ NMR (60 MHz, $CDCl_3$): δ 2.20 (s, 3H, $CH_3C$=O), 5.76 (s, 2 H, $OCH_2O$).

EXAMPLE 15

Acetoxymethyl 2-methacryloyloxyethyl Carbonate

To a solution of acetoxymethyl chloroformate (1.00 g, 0.0066 mol) and 2-hydroxyethyl methacrylate (0.86 g, 0.0066 mol) in methylene chloride (30 ml), pyridine (0.52 g, 0.0066 mol) was added at 0° C. After 10 min at 0° C. and 18 hours at 25° C. the reaction mixture was washed with aqueous hydrochloric acid (100 ml), aqueous saturated sodium hydrogen carbonate (100 ml) and water (100 ml). The solvent was removed under reduced pressure after drying ($MgSO_4$). Flash chromatography (silicagel, hexane/ ethyl acetate (3:2)) gave 1.05 g (65%) of the title product.

$^1H$ NMR (60 MHz, $CDCl_3$): δ 1.95 (d, 3H, $CH_3C$=), 2.10 (s, 3H, $CH_3C$=O), 4.45 (s, 4H, $CH_2O$), 5.55 (m, 1H, $CH_2$=), 5.75 (s, 2H, —$OCH_2O$—), 6.05 (m, 1H, $CH_2$=).

EXAMPLE 16

N-(2-chloromethoxycarbonyloxypropyl)methacrylamide

To a solution of N-(2-hydroxypropyl)methacrylamide[2] (2.86 g, 20 mmol), and pyridine (1.90 g, 24 mmol) in methylene chloride (100 ml), chloromethyl chloroformate (3.87 g, 30 mmol) in methylene chloride (120 ml) was added at 0° C. After 15 min. at 0° C. and 24 hours at 25° C. the reaction mixture was washed with water (5×25 ml). The solvent was removed under reduced pressure after drying ($MgSO_4$), Flash chromatography (silicagel, chloroform) gave 3.30 g (70%) of the title product.

$^1H$ NMR (60 MHz, $CDCl_3$): δ 1.42 (d, 3H, $CH_3$—CH—O), 2.0 (m, 3H, $CH_3C$=), 3.2–4.0 (m, 2H, NH—$CH_2$—CH), 4.8–5.3 (m, 1H, $CH_3$—$CH$—O), 5.6 (d, 2H, $CH_2$=), 5.7 (s, 2H, $CH_2Cl$), 6.1–6.7 (br s, 1H, NH).

EXAMPLE 17 a)  N-(2-acetoxymethoxycarbonyloxypropyl)methacrylamide

A THF solution (30 ml) of TBA acetate (1.21 g, 4 mmol), prepared by freeze-drying an aqueous solution of equimolar TBA-OH and acetic acid, was added to a stirred solution of N-(2-chloromethoxycarbonyloxypropyl) methacrylamide (0.943 g, 4 mmol) from Example 16 above in THF (10 ml) at room temperature. Following stirring for 5 days the solvent was removed under reduced pressure and the residue was dissolved in chloroform (50 ml) and washed with water (5×10 ml). The organic phase was dried (MgSO$_4$) and the solvent removed under reduced pressure. Flash chromatography (silicagel, hexane/ethyl acetate (3:4)) gave 0.486 g (47%) of the title product.

$^1$H NMR (60 MHz, CDCl$_3$): δ 1.4 (d, 3H, CH$_3$—CH—O), 2.0 (m, 3H, CH$_3$C=), 2.2 (s, 3H, CH$_3$C=O), 3.2–4.0 (m, 2H, NH—CH$_2$CH), 4.8–5.3 (m, 1H, CH$_3$—CH—O), 5.6 (d, 2H, CH$_2$=), 5.8 (s, 2H, OCH$_2$O), 6.1–6.7 (br s, 1H, NH).

b) N-(2-acetoxymethoxycarbonyloxypropyl)methacrylamide

To a solution of N-(2-hydroxypropyl)methacrylamide[2] (0.430 g, 3.0 mmol) and pyridine (0.285 g, 3.6 mmol) in methylene chloride (30 ml), acetoxymethyl chloroformate from Example 14 above (0.500 g, 3.3 mmol) in methylene chloride (6 ml) was added at 0° C. After 10 min. at 0° C. and 3 days at 25° C. the reaction mixture was washed with water (100 ml). The solvent was removed under reduced pressure after drying (MgSO$_4$). Flash chromatography (silicagel, hexane/ethyl acetate (3:4)) gave 0.40 g (51%) of the title product.

NMR data are in good agreement with those in (a) above.

EXAMPLE 18

Free Radical Polymerisation of N-(2-acetoxymethoxycarbonyloxypropyl)methacrylamide AIBN (0.0138 g, 0.084 mmol) was added to a solution of N-(2-acetoxymethoxycarbonyloxypropyl)methacrylamide (0.519 g, 2 mmol) from Example 17 above in dry THF (8 ml) at 50° C. under a dry nitrogen atmosphere. After 3 days the solvent was removed under reduced pressure to give 0.439 of a white powder.

$^1$H NMR (200 MHZ, CDCl$_3$): δ 0.8–1.2 (m, 3H, CH$_3$), 1.2–1.4 (m, 3H, CH$_2$—CH(CH$_3$)O), 1.6–2.0 (m, 2H, CH$_2$), 2.1 (s, 3H, CH$_3$CO), 2.9–3.9 (m, 2H, NH—CH$_2$), 4.7–5.0 (m, 1H, CH$_2$CH(CH$_3$)—O), 5.8 (s, 2H, O—CH$_2$—O), 6.2–7.0 (m, 1H, NH).

Size Exclusion Chromatography (SEC): Mw=5411, Mn=2857, Mw/Mn=1.894.

Differential scanning calorimetry (DSC) indicated that Tg=52.91° C.

EXAMPLE 19

N-[2-(1-chloroethoxycarbonyloxy)propylmethacrylamide

To a solution of N-(2-hydroxypropyl)methacrylamide[2] (3.15 g, 22 mmol) and pyridine (2.088 g, 26.4 mmol) in methylene chloride (100 ml ), 1-chloroethyl chloroformate (4.718 g, 33 mmol) in methylene chloride (20 ml) was added at 0° C.). After 10 min. at 0° C. and 5.5 hours at 25° C. the reaction mixture was washed with water (5×40 ml). The solvent was removed under reduced pressure after drying (MgSO$_4$) to give 4.84 g (88%) of the title product.

$^1$H NMR (60 MHz, CDCl$_3$): δ 1.37 (d, 3H, CH$_3$—CH—O), 1.83 (d, 3H, CH$_3$—CH—Cl), 1.97 (m, 3H, CH$_3$C=), 3.3–3.6 (m, 2H, NH—CH$_2$—CH), 4.7–5.3 (m, 1H, CH$_2$—CH(CH$_3$)—O), 5.3 (m, 1H, CH$_2$=), 5.70 (m, 1H, CH$_2$=), 6.0–6.6 (m, 2H, NH+—Cl—CH—CH$_3$).

EXAMPLE 20

N-[2-(1-acetoxyethoxycarbonyloxy)propyl]methacrylamide

A THF solution (100 ml) of TBA acetate (6.93 g, 23 mmol), prepared by freeze-drying an aqueous solution of equimolar TBA-OH and acetic acid, was added to a stirred solution of N-[2-(1-chloroethoxycarbonyloxy)propyl]methacrylamide (4.736 g, 19 mmol) in THF (100 ml) at room temperature. Following stirring for 4 days the solvent was removed under reduced pressure and the residue was dissolved in chloroform (100 ml) and washed with water (5×20 ml). The organic phase was dried (MgSO$_4$) and the solvent removed under reduced pressure. Flash chromatography (silicagel, hexane/ethyl acetate (3:4)) gave 1.29 g (25%) of the title product.

$^1$H NMR (60 MHz, CDCl$_3$): δ 1.3 (d, 3H, CH$_2$—CH(CH$_3$)—O), 1.5 (d, 3H, O—CH(CH$_3$)—O), 2.0 (m,3H, CH$_3$C=), 2.1 (s, 3H, CH$_3$C=O), 3.3–3.6 (m, 2H, NH—CH$_2$—CH), 4.7–5.3 (m, $^1$H, CH$_2$CH(CH$_3$)—O), 5.4 (m, $^1$H, CH$_2$=), 5.7 (m, $^1$H, CH$_2$=), 6.1–6.6 (br s, $^1$H, NH), 6.6–6.9 (m, $^1$H, O—CH(CH$_3$)O).

EXAMPLE 21

Free Radical Polymerisation of N-[2-(1-acetoxyethoxycarbonyloxy)propyl]methacrylamide AIBN (0.0031 g, 0.189 mmol) was added to a solution of N[2-(1-acetoxyethoxycarbonyloxypropyl]methacrylamide (1.23 g, 4.5 mmol) from Example 20 above in dry THF (18 ml) at 50° C. under a dry nitrogen atmosphere. After 3 days the solvent was removed under reduced pressure. Flash chromatography (step gradient, hexane/ethyl acetate (3:4) to methanol) gave 0.96 g of a white powder.

$^1$H NMR (200 MHz, CDCl$_3$): δ 0.8–1.2 (m, 3H, CH$_3$), 1.2–1.4 (m, 3 H, CH$_2$—CH (CH$_3$)—O), 1.5 (d, 3 H, O—CH(CH$_3$)—O), 1.6–2.0 (m, 2H, CH$_2$), 2.0–2.2 (s, 3H, CH$_3$CO), 2.9–3.9 (m, 2H, NH—CH$_2$), 4.7–5.0 (m, $^1$H, CH$_2$CH(CH$_3$)—O), 6.2–7.0 (m, 2H, NH+O—CH(CH$_3$)—O).

Size Exclusion Chromatography (SEC): Mw=1991, Mn=1268, Mp=2105, Mw/Mn=1.548.

Differential scanning calorimetry (DSC) indicated that Tg=51.53° C.

EXAMPLE 22

Methacryloyloxymethyl Benzoate

Potassium tert. butoxide (10.0 g, 0.090 mol) was added to a solution of methacrylic acid (7.75 g, 0.090 mol) in DMF (300 ml). Chloromethyl benzoate[3] (15.0 g, 0.088 mol) was added to the resulting suspension. 18-crown-6 (1.8 g, 6.9 mmol) was then added and the reaction mixture was left with stirring at room temperature for 2 days. The reaction mixture was filtered and the solvent was removed under reduced pressure. The residue was dissolved in chloroform (100 ml) and washed with saturated aqueous Sodium hydrogen carbonate (50 ml) and water (50 ml). The organic phase was dried (MgSO$_4$) and the solvent removed under reduced pressure. Flash chromatography gave 15.9 g (82%) of the title product.

$^1$H NMR (60 MHz, CDCl$_3$): δ 2.00 (s, 3H, CH$_3$C=), 5.65 (m, 1H, CH$_2$=), 6.15 (s, 2H, —OCH$_2$O), 6.35 (m, $^1$H, CH$_2$=), 7.50 (m, 3H, Ph), 8.05 (m, 2H, Ph).

EXAMPLE 23

Polymer from Methacryloyloxymethyl Benzoate

AIBN (0.005 g, 0.03 mmol) was added to a solution of methacryloyloxymethyl benzoate (1.00 g, 4.55 mmol) from Example 22 above in dry THF (8 g) at 60° C. under a dry nitrogen atmosphere. After 24 hours the reaction mixture was cooled to 20° C., and the solvent removed under reduced pressure. The resulting polymer was dissolved in $CH_2Cl_2$ and reprecipitated in methanol. Methanol was separated from the polymer by filtration, resulting in a white powder.

$^1$H NMR (200 MHz, $CDCl_3$): δ 0.85 (m, 3H, $CH_3$), 1.87 (m, 2H, $CH_2$), 5.70 (m, 2H, —$OCH_2O$—), 7.45 (m, 3H, Ph), 8.05 (m, 2H, Ph).

Differential scanning calorimetry (DSC) indicated that Tg=60.98° C.

Size Exclusion Chromatography (SEC): Mw=30281, Mn=11580, Mp=32286, Mw/Mn=2,615.

EXAMPLE 24

Methyl Chloroethyl Carbonate

To a solution of chloroethyl chloroformate (35.74 g, 0.25 mol) and methanol (8.00 g, 0.25 mol) in methylene chloride (300 ml), pyridine (19.78 g, 0.25 mol) was added at 0° C. After 10 min at 0° C. and 2 days at 25° C. the reaction mixture was washed with aqueous hydrochloric acid (100 ml), aqueous saturated sodium hydrogen carbonate (100 ml) and water (100 ml). The solvent was removed under reduced pressure after drying ($MgSO_4$), giving 25.5 g (74%) of the intermediate methyl chloroethyl carbonate as a crude product.

$^1$H NMR (60 MHz, $CDCl_3$): δ 1.85 (d, 3H, $CH_3CH$), 3.80 (s,3H, $CH_{3O}$), 6.50 (q, $^1$H, CH).

EXAMPLE 25

Methyl 1-methacryloyloxyetbyl Carbonate

Potassium tert. butoxide (3.70 g, 0.033 mol) was added to a solution of methacrylic acid (2.84 g, 0.033 mol) in DMF (100 ml). Methyl chloroethyl carbonate (4.55 g, 0.033 mol) from Example 24 above was added to the resulting suspension. 18-crown-6 (0.61 g, 2.3 mmol) was then added and the reaction mixture was left with stirring at room temperature for 3 days. The reaction mixture was filtered and the solvent was removed under reduced pressure. The residue was dissolved in chloroform (100 ml) and washed with saturated aqueous sodium hydrogen carbonate (50 ml) and water (50 ml). The organic phase was dried ($MgSO_4$) and the solvent removed under reduced pressure. Flash chromatography gave 4.46 g (72%) of the title product.

$^1$H NMR (60 MHz, $CDCl_3$): δ 1.65 (d, 3H CH3CH), 2.00 (s, 3H, $CH_3C$=), 3.90 (s, 3H, $CH_3O$),5.65 (m, $^1$H, $CH_2$=), 6.25 (m, $^1$H, $CH_2$=), 6.90 (q, $^1$H, $CHCH_3$).

EXAMPLE 26

Free Radical Polymerisation of Methyl 1-methacryloyloxyethyl Carbonate

AIBN (0.005 g, 0.03 mmol) was added to a solution of methyl 1-methacryloyloxyethyl carbonate (1.0 g, 5.0 mmol) in dry THF (Sg) at 60° C. under a dry nitrogen atmosphere. After 24 hours the reaction mixture was cooled to 20° C., and the solvent removed under reduced pressure. The resulting polymer was dissolved in $CH_2Cl_2$ and reprecipitated in methanol. Methanol was separated from the polymer by filtration, resulting in a white powder.

$^1$H NMR (200 MHz, $CDCl_3$): δ 0.90 (m, 3H, $CH_3$), 1.45 (s, 3H, $CH_3CH$), 1.87 (m, 2H, $CH_2$), 3.80 (s, 3H, $CH_3O$), 6.65 (bs, $^1$H, $CHCH_3$).

Size Exclusion Chromatography (SEC): Mw=16033, Mn=6641, Mp=16192, Mw/Mn=2.41.

Differential scanning calorimetry (DSC) indicated that Tg=57.65° C.

EXAMPLE 27

Free Radical Emulsion Homopolymerisation of Benzyl Methacryloyloxymethyl Carbonate A solution of sodium dodecyl sulphate (1.6—$10^{-2}$ mmol) in deoxygenated water (6.0 ml) was added to a 50 ml two necked round bottom flask fitted with magnetic stirring bar and condenser. To the solution, potassium metabisulphite (0.015 g, $6.7\times10^{-2}$ mmol) dissolved in deoxygenated water (1.0 ml), and benzyl methacryloyloxymethyl carbonate (2.0 g, 8.0 mmol) were added. The reaction mixture was heated to a temperature of 60° C. To the heated reaction mixture potassium persulphate ($1.25\times10^{-3}$ g, $4.6\times10^{-3}$ mmol) was added and the reaction allowed to proceed. After approximately 5 hours the polymerisation was stopped and the polymer emulsion was added dropwise to a large excess of methanol (non-solvent). The polymer was then filtered and washed with methanol and water. This procedure was repeated a total of three times in order to purify the polymer. The polymer was then collected and dried under vacuum to remove any solvent impurities. Some of the stable emulsion was not extracted as above but saved for particle size analysis by light microscopy. The size of the emulsion particles was estimated by optical microscopy and found to be just under 1μm in diameter.

EXAMPLE 28

Methacryloyloxymethyl Acetate

Potassium tert. butoxide (5.0 g, 0.045 mol ) was added to a solution of methacrylic acid (3.87 g, 0.045 mol) in DMF (150 ml). Chloromethyl acetate[3] (4.86 g, 0.045 mol) was added to the resulting suspension. 18-crown-6 (0.9 g, 3.45 mmol) was then added and the reaction mixture was left with stirring at room temperature for 4 days. The reaction mixture was filtered and the solvent was removed under reduced pressure. The residue was dissolved in chloroform (100 ml) and washed with saturated aqueous sodium hydrogen carbonate (50 ml) and water (50 ml). The organic phase was dried ($MgSO_4$) and the solvent removed under reduced pressure. Flash chromatography gave 5.19 g (75 %) of the title product.

$^1$H NMR (60 MHz, $CDCl_3$): δ 2.00 (s, 3H, $CH_3C$=), 2.18 (s, 3H, $CH_3C$=O), 5.70 (m, $^1$H, $CH_2$=), 5.85 (s, 2H, —$OCH_2O$—), 6.25 (m, $^1$H, $CH_2$=)

EXAMPLE 29

Butyl Acryloyloxymethyl Carbonate

Potassium tert. butoxide (5.84 g, 0.052 mol) was added to a solution of acrylic acid (4.47 g, 0.045 mol) in DMF (220 ml). Butyl chloromethyl carbonate (6.5 g, 0.052 mol) in DMF (150 ml) was added to the resulting suspension.

18-crown-6 (0.6 g) was then added and the reaction mixture was left with stirring at room temperature for 2 days. The reaction mixture was filtered and the solvent was removed under reduced pressure. The residue was dissolved in chloroform (100 ml) and washed with saturated aqueous sodium hydrogen carbonate (50 ml) and water (50 ml). The organic phase was dried (MgSO$_4$) and the solvent removed under reduced pressure. Flash chromatography gave 4.57 g of the title product.

$^1$H NMR (60 MHz, CDCl$_3$): δ 0.80 (t, 3H, CH$_3$CH$_2$), 1.28 (m, 2H, CH$_2$), 1.60 (m, 2H, CH$_2$), 4.15 (t, CH$_2$O), 5.78 (s, 2H, OCH$_2$O), 5.88 (dd, 1H, CH$_2$=), 6.1 (dd, 1H, CH$_2$=), 6.45 (dd, 1H, CH$_2$=CH—).

EXAMPLE 30

Polymer from Methacryloyloxymethyl Acetate

AIBN (0.005 g, 0.03 mmol) was added to a solution of methacryloyloxymethyl acetate (Example 28, 1.00 g, 4.55 mmol) in dry THF (8 g) at 60° C. under a dry nitrogen atmosphere. After 24 hours the reaction mixture was cooled to 20° C., and the solvent removed under reduced pressure. The resulting polymer was dissolved in CH$_2$Cl$_2$ and reprecipitated in methanol. Methanol was separated from the polymer by filtration, resulting in a white powder.

Differential scanning calorimetry (DSC) indicated that Tg=54.99° C.

Size Exclusion Chromatography (SEC): Mw=184678, Mn=2446, Mp=54732, Mw/Mn=7.56

EXAMPLE 31

Polymer from Ethyl 1-methacryloyloxyethyl Carbonate, Emulsion Polymerisation

A mixture of sodium dodecylsulphate (6.5 mg, 0.023 mmol) in water (2.40 ml) and potassium metabisulphite (6.3 mg, 0.028 mmol) in water (0.82 ml) was heated to 60° C. under nitrogen atmosphere, before ethyl 1-methacryloyloxyethyl carbonate (Example 10, 0.617 g, 3.10 mmol) was added. The polymerisation was initiated by adding potassium persulphate (0.54 mg, 0.002 mmol) in water (0.25 ml). The polymerisation was permitted to proceed for 20 hours at 60° C. under nitrogen atmosphere, before cooling to 20° C.

EXAMPLE 32

1-Chloro-1-phenylmethyl Vinyl Carbonate

Vinyl chloroformate (3.0 g, 0.028 mol) and benzaldehyde (4.14 g. 0.039 mol) were dissolved in 1,2-dichloroethane (30 ml) and pyridine (0.1 g, 1.28 mol) was added dropwise to the stired solution. The solution was stirred for 1 day at 80° C., washed with water (25 ml), and the aqueous phase was back extracted with methylene chloride (25 ml). The combined organic phases were dried (MgSO$_4$) and concentrated to give 3.0 g (50%) of the title product.

$^1$H NMR (60 MHz, CDCl$_3$): δ 4.55 (dd, 1H, CH$_2$=), 4.95 (dd, 1H, CH$_2$=), 7.05 (dd, $^1$H, CH$_2$=CH—), 7.25 (s, 1H, CH—Ph), 7.40 (m, 5H, Ph).

EXAMPLE 33

1-Acetoxy-1-phenylmethyl Vinyl Carbonate

Silver acetate (2.0 g, 0.012 mol) was added to a solution of 1-chloro-1-phenylmethyl vinyl carbonate from Example 32 (2.50 g, 0.012 mol) in DMF (60 ml). The reaction mixture was left with stirring at room temperature for 12 hours. The reaction mixture was filtered and the solvent was removed under reduced pressure. The residue was purified by flash chromatography (silicagel, methylene chloride) to give 0.56 g, (20%) of the title product.

$^1$H NMR (60 MHz, CDCl$_3$): δ 2.24 (s, 3H, CH$_3$C=O), 4.60 (dd, 1H, CH$_2$=), 4.95 (dd, 1H, CH$_2$=), 7.00 (dd, 1H, CH=), 7.50 (m, 5H, Ph), 8.00 (s, 1H, —CH—Ph).

EXAMPLE 34

Free Radical Polymerisation of 1-acetoxy-1-phenylmethyl Vinyl Carbonate

AIBN (0.005 g, 0.03 mol) is added to a solution of 1-dimethylformamide, acetoxy-1-phenylmethyl vinyl carbonate from Example 33 (1.0 g) in dry THF (8 ml) at 60° C. under a dry nitrogen atmosphere. After 12 hours the solvent is removed under reduced pressure. The resulting polymer is dissolved in CH$_2$Cl$_2$ and reprecipitated in a suitable solvent. The polymer is separated from the solvent by filtration, resulting in a white powder.

EXAMPLE 35

O-Benzoyloxymethyl-S-ethyl Carbonothioate

O-Chloromethyl-S-ethyl carbonothioate$^1$ (5.73 g, 0.037 mol) in DMF (20 ml) was added to a solution of potassium benzoate (5.94 g, 0.037 mol), and 18-crown-6 (0.485 g, 1.85 mmol) in DMF (130 ml) was then added and the reaction mixture was left with stirring at room temperature for 24 hours. The solvent was removed under reduced pressure. The residue was dissolved in chloroform (150 ml) and washed with water (5×20 ml) and dried (MgSO$_4$). The solvent was removed under reduced pressure, purified by flash chromatography (silicagei, chloroform) to give 7.16 g (81%) of the title product.

$^1$H NMR (60 MHz, CDCl$_3$): δ 1.3 (t, 3H, CH$_3$), 2.9 (q, 2H, CH$_2$CH$_3$), 6.1 (s, 2H, OCH$_2$O), 7.3–7.7 (m, 3H, Ph), 8.0–8.2 (m, 2H, Ph).

EXAMPLE 36

Benzoyloxymethyl Chloroformate

SO$_2$Cl$_2$ (4.03 g, 0.030 mol) is added to O-benzoyloxymethyl-S-ethyl carbonothioate from Example 35 (7.16 g, 0.030 mol) at 0°–5° C. with stirring during 15 min. followed by stirring at room temperature for 2 hours. Evaporation of EtSCl at room temperature and 11 mmHG gave a yellow liquid. Yield: 5.30 g (83%). $^1$H NMR (60 MHz, CDCl$_3$): δ 6.1 (s, 2H, OCH$_2$O), 7.3–7.7 (m, 3H, Ph), 8.0–8.2 (m, 2H, Ph).

EXAMPLE 37

N-(3-aminopropy)methacrylamide

Methacryloyl chloride (8.0 g, 0.078 mmol) in methylene chloride (10 ml) was added to a solution of 1,3-diaminopropane (35 ml) in methylene chloride (200 ml) at 0° C.

After 15 min. stirring at 0° C. and 16 hours at 25° C. the reaction mixture was filtered and concentrated under reduced pressure. The residue was purified by flash chromatography (silicagel, chloroform/methanol (8:2)) to give (72%) of the title compound.

$^1$H NMR (60 MHz, CDCl$_3$/d$_6$-acetone): δ 1.70 (m, 2H, CH$_2$CH$_2$CH$_2$), 2.00 (s, 3H, CH$_3$C), 2.30 (s, 2H, NH$_2$), 2.98 (m, 2H CH$_2$NH$_2$), 3.35 (m, 2H, NHCH$_2$), 5.35 (m, 1H, CH$_2$=), 5.80 (m, 1H, CH$_2$=), 7.45 (m, 1H, NH).

EXAMPLE 38

N-(3-methacrylamidoylpropyl)-O-(benzoyloxymethyl)carbamate

Benzoyloxymethyl chloroformate (1 equiv.) is added to a 0.1M solution of N-(3-aminopropyl)methacrylamide (2 equiv.) in methylene chloride at 0° C. After 15 min. at 0° C. and a suitable time at 25° C. the reaction mixture is filtered and concentrated to dryness under reduced pressure. The residue is purified by flash chromatography giving the wanted N-(3-methacrylamidoyl-propyl)-O-(benzoyloxymethyl) carbamate.

EXAMPLE 39

Free Radical Solution Polymerisation of N-(3-methacrylamidoylpropyl)-O-(benzoyloxymethyl) Carbamate AIBN (3/100 equiv.) is added to a 0.5M solution of N-(3-methacrylamidoylpropyl)-O-(benzoyloxymethyl) carbamate (1 equiv.) in THF at 60° C. After 24 hours at 60° C. the reaction mixture is cooled to 25° C. and concentrated to dryness under reduced pressure. SEC analysis of the crude product indicates the formation of polymer.

EXAMPLE 40

Chloromethyl Morpholine-4-carboxylate

Morpholine (1 equiv.) is slowly added to a 0.1M solution of chloromethyl chloroformate (10 equiv.) in methylene chloride at low temperature. After 15 min at low temperature and a suitable time at 25° C. the reaction mixture is filtered and concentrated to dryness under reduced pressure. The residue is purified by flash chromatography giving chloromethyl morpholine-4-carboxylate.

EXAMPLE 41

Methacryloyloxymethyl Morpholine-4-carboxylate

Chloromethyl morpholine-4-carboxylate (1 equiv.) is added to a 0.1M solution of the potassium salt of methacrylic acid (1.1 equiv.) and 18-crown-6 (2/100 equiv.) in DMF at 0° C. After 15 min at 0° C. and a suitable time at elevated temperature the reaction mixture is filtered and concentrated to dryness under reduced pressure. The residue is purified by flash chromatography giving the wanted methacryloyloxymethyl morpholine-4-carboxylate.

EXAMPLE 42

Free Radical Polymerisation of Methacryloyloxymethyl Morpholine-4-carboxylate

AIBN (3/100 equiv.) is added to a 0.5M solution of methacryloyloxymethyl morpholine-4-carboxylate (1 equiv.) in THF at 60° C. After 24 hours at 60° C. the reaction mixture is cooled to 25° C. and concentrated to dryness under reduced pressure. Size Exclusion Chromatography (SEC) indicates formation of polymer.

EXAMPLE 43

O-Methacryloyloxymethyl-S-ethyl Carbonothioate

O-Chloromethyl-S-ethyl carbonothioate[1] (1 equiv.) is added to a 0.1M solution of the potassium salt of methacrylic acid (1 equiv.) and 18-crown-6 (2/100 equiv.) in DMF at 0° C. After 15 min at 0° C. and a suitable time at elevated temperature the reaction mixture is filtered and concentrated to dryness under reduced pressure. The residue is purified by flash chromatography giving the wanted O-methacryloyloxymethyl-S-ethyl carbonothioate.

EXAMPLE 44

Free Radical Polymerisation of O-methacryloyloxymethyl-S-ethyl Carbonothioate

AIBN (3/100 equiv.) is added to a 0.5M solution of O-methacryloyloxymethyl-S-ethyl carbonothioate (1 equiv.) in THF at 60° C. After 24 hours at 60° C. the reaction mixture is cooled to 25° C. and concentrated to dryness under reduced pressure. Size Exclusion Chromatography (SEC) indicates formation of polymer.

EXAMPLE 45

Free Radical Solution Co-polymerisation of N-(2-hydroxypropyl)methacrylamide with N-(2-acetoxyrmethoxycarbonyloxypropyl) methacrylamide N-(2-hydroxypropyl)methacrylamide[2] (0.430 g, 3.0 mmol) and N-(2-acetoxymethoxycarbonyloxypropyl)methacrylamide (Example 17, 0.778 g, 3.0 mmol) were dissolved in tetrahydrofuran (10 ml) and heated to 55° C. AIBN (0.0207 g, 0.126 mmol) was added, and the mixture was stirred at 55° C. for 3 days to give a clear jelly. This was dissolved in tetrahydrofuran and the solvent evaporated under reduced pressure to give a white powder (1.33 g).

Size Exclusion Chromatography (SEC) indicated formation of polymer.

EXAMPLE 46

Enzyme-catalyzed Hydrolysis of Polymer from Methacryloyloxymethyl Benzoate 50 mg samples of the polymer (Example 23), as finely divided powder, and 20 ml 0.9% aqueous NaCl were added to each of three reaction vials. To one of the vials was also added 0.1 ml esterase from porcine liver in 3.2M (NH$_4$)$_2$SO$_4$, (Sigma E-3128, 250U). To another of the vials was added 0.1 ml 3.2M (NH$_4$)$_2$SO$_4$. Using a pH-stat (Radiometer), the pH within each of the vials was kept constant at 8.0 by adding 0.1M NaOH. By recording the consumption of NaOH, the rates of hydrolysis were calculated. Over 45 hours at 37° C., the hydrolysis of the polymer with esterase was found to be 11 times faster than the control with $(NH_4)_2SO_4$ without esterase. In the control containing polymer in 0.9% NaCl no hydrolysis was found (see FIG. 1 of the accompanying drawing).

TABLE 5

Consumption of 0.1M NaOH in vial containing polymer and esterase with 0.1 ml 3.2M $(NH_4)_2SO_4$ in 20 ml 0.9% NaCl-solution:

| Time (min) | pH | Volume 0.1M NaOH added (ml) |
|---|---|---|
| 0 | 8.00 | 0.000 |
| 100 | 8.00 | 0.080 |
| 220 | 8.00 | 0.142 |
| 355 | 8.00 | 0.239 |
| 2670 | 8.00 | 1.101 |
| 2710 | 8.00 | 1.105 |

TABLE 6

Consumption of 0.1M NaOH in control containing 0.1 ml 3.2M $(NH_4)_2SO_4$ in 20 ml 0.9% NaCl-solution:

| Time (min) | pH | Volume 0.1M NaOH added (ml) |
|---|---|---|
| 0 | 8.00 | 0.000 |
| 120 | 8.00 | 0.012 |
| 240 | 8.00 | 0.030 |
| 4316 | 8.00 | 0.130 |

TABLE 7

Consumption of 0.1M NaOH in control containing polymer in 20 ml 0.9% NaCl-solution:

| Time (min) | pH | Volume 0.1M NaOH added (ml) |
|---|---|---|
| 0 | 8.4 | 0 |
| 115 | 8.0 | 0.002 |
| 250 | 8.0 | 0.002 |
| 300 | 8.0 | 0.002 |
| 1600 | 8.0 | 0.002 |

REFERENCES

1. Folkmann M., Lund F. J., *Synthesis* 1990, 1159
2. Stroholm J., Kopecek J., *Angew. Macromol. Chemie* 70, 1978, 109
3. Benneche T., Strande P., Wiggen U., *Acta Chem. Scand.* 43, 1988, 74

We claim:

1. Biodegradable non-crosslinked polymers of low or zero water-solubility comprising a non-polypeptide polymer backbone carrying side chains, at least a proportion of the said side chains containing lipophilic moieties bonded to the polymer backbone by way of methylene diester units of formula (I)

(where $R^1$ and $R^2$, which may be the same or different, each represent a hydrogen atom or a carbon-attached monovalent organic group or $R^1$ and $R^2$ together form a carbon-attached divalent organic group), whereby the said lipophilic moieties are biodegradatively cleavable to yield a water-soluble polymer.

2. Polymers as claimed in claim 1 containing units of formula (II)

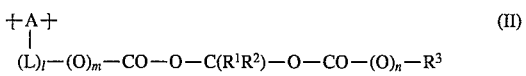

(where A represents a repeating unit of a nonpolypeptide polymer backbone chain; L represents a linking group; l, m and n, which may be the same or different, are each zero or 1; $R^1$ and $R^2$ are as defined in claim 1 and $R^3$ represents a lipophilic organic group).

3. Polymers as claimed in claim 2 wherein the repeating units A and any comonomer units contain 1–6 carbon atoms optionally interrupted by one or more heteroatoms selected from oxygen, nitrogen and sulphur and/or substituted by one or more substituents comprising such heteroatoms.

4. Polymers as claimed in claim 3 wherein A represents ethylene or propylene.

5. Polymers as claimed in claim 2 wherein L is a $C_{1-3}$ alkylene group optionally terminating in and/or interrupted by one or more oxy, carbonyl, oxycarbonyl, imino or iminocarbonyl groups.

6. Polymers as claimed claim 1 which are biodegradable to yield a water-soluble polyvinyl alcohol, polyacrylic acid, polymethacrylic acid, polyhydroxyalkyl acrylate or methacrylate, polysaccharide, polyester, polyether, polyamide, polyurethane or epoxy polymer.

7. Polymers as claimed in claim 2 wherein $R^1$ and $R^2$ (when other than hydrogen) and $R^3$ are selected from aliphatic groups having up to 10 carbon atoms, cycloalkyl groups having up to 10 carbon atoms, araliphatic groups having up to 20 carbon atoms, aryl groups having up to 20 carbon atoms, heterocyclic groups having up to 20 carbon atoms and one or more heteroatoms selected from oxygen, sulphur and nitrogen, and any of the preceding groups carrying one or more functional substituents and/or, in the case of $R^3$, interrupted and/or terminated by a heteroatom selected from oxygen, nitrogen and sulphur.

8. Polymers as claimed in claim 7 wherein $R^1$ and $R^2$ are each selected from hydrogen atoms and $C_{1-4}$ alkyl groups and $R^3$ is selected from lower alkyl, phenyl and phenyl lower alkyl.

9. Polymers as claimed in claim 2 in the form of surgical implants, soft tissue prostheses, sponges, films, wound dressings, flexible sheets, containers and delayed release formulations for drugs and agricultural chemicals, particulate imaging agents or plasticisers.

10. A process for the preparation of a polymer as claimed in claim 1 which comprises either (A) reaction of a preformed water-soluble polymer with a reagent serving to introduce the desired lipophilic methylene diester side chain or (B) polymerisation of a functional monomer which carries the desired lipophilic methylene diester side chain.

11. A process according to (B) of claim 10 wherein free radical polymerisation is effected.

12. Polymers as claimed in claim 3 wherein L is a $C_{1-3}$alkylene group optionally terminating in and/or interrupted by one or more oxy, carbonyl, oxycarbonyl, imino or iminocarbonyl groups.

13. Polymers as claimed in claim 4 wherein L is a $C_{1-3}$alkylene group optionally terminating in and/or interrupted by one or more oxy, carbonyl, oxycarbonyl, imino or iminocarbonyl groups.

14. Polymers as claimed in claim 2 which are biodegradable to yield a water-soluble polyvinyl alcohol, polyacrylic acid, polymethacrylic acid, polyhydroxyalkyl acrylate or methacrylate, polysaccharide, polyester, polyether, polyamide, polyurethane or epoxy polymer.

15. Polymers as claimed in claim 3 which are biodegradable to yield a water-soluble polyvinyl alcohol, polyacrylic acid, polymethacrylic acid, polyhydroxyalkyl acrylate or methacrylate, polysaccharide, polyester, polyether, polyamide, polyurethane or epoxy polymer.

16. Polymers as claimed in claim 4 which are biodegradable to yield a water-soluble polyvinyl alcohol, polyacrylic acid, polymethacrylic acid, polyhydroxyalkyl acrylate or methacrylate, polysaccharide, polyester, polyether, polyamide, polyurethane or epoxy polymer.

17. Polymers as claimed in claim 5 which are biodegradable to yield a water-soluble polyvinyl alcohol, polyacrylic acid, polymethacrylic acid, polyhydroxyalkyl acrylate or methacrylate, polysaccharide, polyester, polyether, polyamide, polyurethane or epoxy polymer.

18. Polymers as claimed in claim 3 wherein $R^1$ and $R^2$, when other than hydrogen, and $R^3$ are selected from the group consisting of aliphatic groups having up to 10 carbon atoms, cycloalkyl groups having up to 10 carbon atoms, araliphatic groups having up to 20 carbon atoms, and one or more heteroatoms selected from oxygen, sulphur, and nitrogen, and any of the preceding groups carrying one or more functional substituents and/or, in the case of $R^3$, interrupted and/or terminated by a heteroatom selected from the group consisting of oxygen, nitrogen and sulphur.

19. Polymers as claimed in claim 4 wherein $R^1$ and $R^2$, when other than hydrogen, and $R^3$ are selected from the group consisting of aliphatic groups having up to 10 carbon atoms, cycloalkyl groups having up to 10 carbon atoms, araliphatic groups having up to 20 carbon atoms, and one or more heteroatoms selected from oxygen, sulphur, and nitrogen, and any of the preceding groups carrying one or more functional substituents and/or, in the case of $R^3$, interrupted and/or terminated by a heteroatom selected from the group consisting of oxygen, nitrogen and sulphur.

20. Polymers as claimed in claim 18 wherein $R^1$ and $R^2$ are each hydrogen atoms or $C_{1-4}$ alkyl groups and $R^3$ is lower alkyl, phenyl or phenyl lower alkyl.

21. Polymers as claimed in claim 1 wherein the lipophilic moieties are biodegradatively cleaved from the polymer backbone by esterase enzyme degradation of the methylene diester units.

* * * * *